United States Patent [19]
Montanari et al.

[11] Patent Number: 5,747,513
[45] Date of Patent: May 5, 1998

[54] DERIVATIVES OF 2-AMINO-1,2,3,4-TETRAHYDRONAPHTHALENE ACTIVE ON THE CARDIOVASCULAR SYSTEM

[75] Inventors: Stefania Montanari; Paolo Cavalleri; Francesco Santangelo, all of Milan, Italy

[73] Assignee: Zambon Group, S.P.A., Vicenza, Italy

[21] Appl. No.: 605,136

[22] PCT Filed: Sep. 7, 1994

[86] PCT No.: PCT/EP94/02981

§ 371 Date: Apr. 30, 1996

§ 102(e) Date: Apr. 30, 1996

[87] PCT Pub. No.: WO95/07885

PCT Pub. Date: Mar. 23, 1995

[30] Foreign Application Priority Data

Sep. 14, 1993 [IT] Italy ............... MI93A1973

[51] Int. Cl.$^6$ ............... C07D 233/84; A61K 31/38
[52] U.S. Cl. ............... 514/351; 514/445; 514/398; 514/380; 514/510; 514/649; 546/300; 548/243; 548/324.1; 549/65; 560/129; 558/190
[58] Field of Search ............... 549/65, 68, 72, 549/74; 546/300, 304, 315, 328, 329; 548/331.5, 335.5, 340.1, 243, 245, 246, 247, 324.1; 514/351, 445, 398, 380, 510, 649; 560/129; 558/190

[56] References Cited

U.S. PATENT DOCUMENTS

| | | | |
|---|---|---|---|
| 5,013,760 | 5/1991 | Farmer et al. | 514/649 |
| 5,118,704 | 6/1992 | Minaskanian et al. | 514/416 |

FOREIGN PATENT DOCUMENTS

| | | |
|---|---|---|
| 0142283 | 5/1985 | European Pat. Off. |
| 0321968 | 6/1989 | European Pat. Off. |
| 9100727 | 1/1991 | WIPO |
| 9319036 | 9/1993 | WIPO |

Primary Examiner—Johann Richter
Assistant Examiner—Laura Cross
Attorney, Agent, or Firm—Watson Cole Stevens Davis, P.L.L.C.

[57] ABSTRACT

Compounds of the formula:

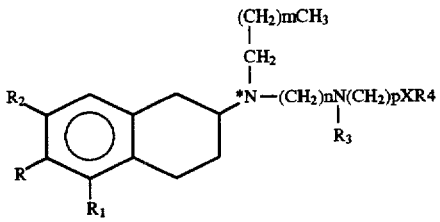

wherein R is a hydrogen atom or an OY group; $R_1$ is a hydrogen atom or in OY' group; $R_2$ is a hydrogen atom or an OY" group; provided that at lent one among R, $R_1$ and $R_2$ is hydrogen but R, $R_1$, and $R_2$ are not contemporaneously hydrogen atoms and $R_1$ and $R_2$ are not contemporaneously OY' or OY" groups respectively; m is an integer 1 or 2; n is an integer 3 to 8; p is an integer 2, 3, or 4; $R_3$ is a hydrogen atom or a $C_1$–$C_4$ alkyl; $R_4$ is a phenyl optionally substituted by halogen atom or a $C_1$–$C_3$ alkyl or alkoxy group or a 5- or 6- membered heteroaryl containing one or more heteroatoms selected from oxygen, nitrogen and sulphur, optionally substituted by halogen atoms, hydroxy groups, $C_1$–$C_3$ alkyl or alkoxy groups; X is $CH_2$, NH, S, SO, $SO_2$, CO, $CF_2$, O and, when $R_4$ is a 5- or 6- membered heteroaryl, X can be also a single bond. Pharmaceutically acceptable salts are described. The compounds of formula (I) are useful in the treatment of arterial hypertension and heart failure, of renal insufficiency, of peripheral arteriopathies and of cerebrovascular insufficiencies.

10 Claims, No Drawings

DERIVATIVES OF 2-AMINO-1,2,3,4-TETRAHYDRONAPHTHALENE ACTIVE ON THE CARDIOVASCULAR SYSTEM

This application is a 371 of PCT/EP94/02981 filed Sep. 7, 1994.

The present invention relates to compounds active on the cardiovascular system and, in particular, it relates to derivatives of 2-amino-1,2,3,4-tetrahydronaphthalene and to their use in therapeutic field.

It is known that some hydroxylated 2-amino-1,2,3,4-tetrahydronaphthalenes are agonists of dopaminergic receptors and several studies about the structure-activity relationship have been carried out to determine the structure characteristics able to ensure the best dopaminergic activity and to avoid, at the same time, the undesired effects of dopamine.

An interesting review of these studies is collected in a paper published by H. E. Katerinopoulos and D. I. Schuster on Drugs of the Future, vol. 12(3), pages 223–253, (1987).

In spite of the various studies, however, the topology of dopaminergic receptors has not been yet explained and a series of receptor models has been proposed in the last ten years.

In the field of the compounds structurally related to dopamine and/or to 2-amino-1,2,3,4-tetrahydronaphthalene, some authors have found that the presence of a $C_3$–$C_4$ alkyl group on the amino function is one of the requirements for dopaminergic activity while the structural requirements of the second substituent on the amino group have not yet been found.

Nevertheless, there are several examples in literature showing how the structural features of the two substituents can be, in practice, extremely variable and how small changes of the molecule can affect the pharmacological activity both quantitatively and qualitatively in a relevant manner.

Among the most significant examples the following are cited. European patent application No. 72061 (Fisons) describes, among the others, dopamines and amino-tetrahydronaphthalenes having a mono- or di-substituted portion of formula

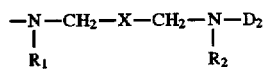

wherein

X is a —$(CH_2)_n$— chain, optionally substituted by hydroxy; n is an integer between 1 and 7; $R_1$ and $R_2$, the same or different, are hydrogen, alkyl or phenyl; $D_2$ is hydrogen, alkyl, phenyl, alkyl substituted by one or more hydroxy, pyridyl, phenyl; alkyl substituted by phenyl substituted, in turn, by halogen, alkyl, amino, alkoxy or nitro; or $D_2$ may be the phenylethyl moiety of a dopamine or a hydroxy-1,2,3,4-tetrahydronaphthyl moiety.

Among the compounds described in European patent application No. 72061, the compound of formula

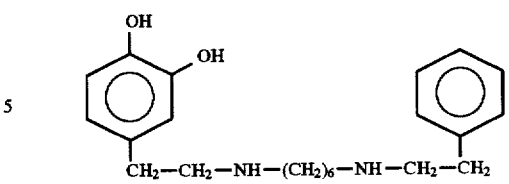

whose international non-proprietary name is dopexamine (The Merck Index—XI ed., No. 3418, page 538) is the only compound, as far as we know, which has been developed and used in the acute treatment of heart failure.

It is significant that dopexamine, notwithstanding it was the compound of choice among the several compounds described and exemplified in European patent application No. 72061, is an agonist of dopaminergic receptors less active than dopamine and, like dopamine itself, it is not absorbed when administered by oral route [A. Fitton and P. Benfield, Drugs, 39(2), 308–330, (1990)].

European patent application No. 142283 (Fisons) describes a class of compounds which are analogs of dopexamine and in which the amino group of the dopamine moiety is still secondary.

In literature, there are several compounds with a catecholamine structure having the aim of keeping the favorable properties of dopexamine, also when administered by oral route, or of increasing the selectivity towards both dopaminergic receptors.

As far as we know, however, none of these compounds has shown all the required characteristics.

For the specific treatment of hypertension and heart failure still exists among physicians the need of drugs which are dopaminergic agonists more potent than dopamine and not selective towards a particular dopaminergic receptor subtype ($D_1$ or $D_2$), which do not interact with other receptor systems and, at the same time, which do not show either the side effects or the disadvantageous therapeutical aspects of dopamine, such as the lack of absorption by oral route and the short action (Goodman and Gilman's—"The Pharmacological Basis of Therapeutics"—VII ed., pages 161–163).

In this connection, it is interesting European patent application No. 321968 (SIMES Societa Italiana Medicinali e Sintetici S.p.A. now Zambon Group S.p.A.), which describes compounds of formula

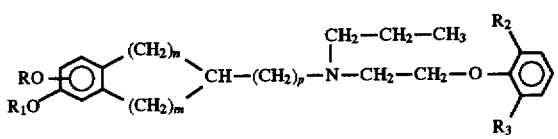

wherein

R and $R_1$, the same or different, are hydrogen or acyl deriving from an aliphatic, aromatic or heteroaromatic carboxylic acid, from a carbonic or carbamic acid or from phosphoric acid; n and p are integers selected between 0 and 1; m is an integer selected among 1, 2, 3 and 4 so that n+p=1 and m+n is 2, 3 or 4; $R_2$ and $R_3$, the same or different, are hydrogen, halogen, alkyl or alkoxy.

These compounds are $D_1$ and $D_2$ dopaminergic receptor agonists, show contemporaneously an $\alpha_1$-antagonist effect, do not interact with other receptor systems, but they must be transformed into suitable prodrugs to be active by oral administration.

We have now found compounds which are dopaminergic receptor agonists more potent than dopamine, which are substantially free from interactions with other receptor systems and, above all, which are absorbed by oral route and have a long action.

Therefore, object of the present invention are the compounds of formula $$\text{*N—(CH}_2)_n\text{—N—(CH}_2)_p\text{—X—R}_4 \quad (I)$$

with substituents (CH$_3$)$_m$—CH$_3$, CH$_2$, R$_2$, R, R$_1$, R$_3$ on a tetrahydronaphthalene ring system.

wherein

R is a hydrogen atom or an OY group;

R$_1$ is a hydrogen atom or an OY' group;

R$_2$ is a hydrogen atom or an OY" group;
provided that at least one among R, R$_1$ and R$_2$ is hydrogen but R, R$_1$ and R$_2$ are not contemporaneously hydrogen atoms and R$_1$ and R$_2$ are not contemporaneously OY' or OY" groups respectively;

Y, Y' and Y", the same or different, are a hydrogen atom or an acyl group deriving from an optionally substituted aliphatic, aromatic or heteroaromatic carboxylic acid, from an optionally substituted carbonic or carbamic acid or from a phosphoric acid of formula $$R_5\text{—O—}\underset{\underset{\text{OH}}{|}}{\overset{\overset{\text{O}}{\|}}{P}}$$

wherein

R$_5$ is a hydrogen atom, a C$_1$–C$_4$ alkyl optionally substituted by one or more groups selected among hydroxy, alkoxy, acyloxy, amino, carboxy and alkoxycarbonyl; or a phenyl;

m is an integer selected between 1 and 2;

n is an integer comprised among 3 and 8;

p is an integer comprised among 2 and 4;

R$_3$ is a hydrogen atom or a C$_1$–C$_4$ alkyl;

R$_4$ is a phenyl optionally substituted by alogen atoms, C$_1$–C$_3$ alkyl or alkoxy groups or a 5- or 6-membered heteroaryl containing one or more heteroatoms selected among oxygen, nitrogen and sulphur, optionally substituted by halogen atoms, hydroxy groups, C$_1$–C$_3$ alkyl or alkoxy groups;

X is CH$_2$, NH, S, SO, SO$_2$, CO, CF$_2$, O and, when R$_4$ is a 5- or 6-membered heteroaryl, X can be also a single bond;

provided that when X is O, R$_4$ is different from phenyl and when X is CH$_2$, R$_4$ is different from phenyl or pyridyl;

the asterisk marks an asymmetric carbon atom;

and pharmaceutically acceptable salts thereof.

The compounds of formula I have at least an asymmetric center, marked by an asterisk, and they can be in the form of stereoisomers.

Object of the present invention are the compounds of formula I in the form of stereoisomeric mixtures as well as in the form of single stereoisomers.

The compounds of formula I are dopaminergic receptor agonists active also by oral route and with a long action and they are useful in therapy in the cardiovascular field, in particular for the treatment of arterial hypertension and heart failure, of renal insufficiency, in the treatment of peripheral arteriopathies and of cerebrovascular insufficiencies.

Specific examples of alkyl or alkoxy groups are methyl, ethyl, n.propyl, i.propyl, n.butyl, i.butyl, sec.butyl, ter.butyl, methoxy, ethoxy, n.propoxy and i.propoxy.

Specific examples of 5- or 6-membered heteroaryl containing one or more heteroatoms selected among oxygen, nitrogen and sulphur are pyridyl, pyrimidyl, imidazolyl, thiazolyl, furyl, thienyl, oxazolyl, isoxazolyl, piperazinyl and pyrrolyl.

The term "acyl group deriving from an aliphatic carboxylic acid" stands for an acyl radical deriving from a linear or branched aliphatic carboxylic acid having from 1 to 6 carbon atoms, optionally substituted by phenyl, halogen or alkoxy groups; specific examples are acyl groups deriving from the following acids: formic, acetic, propionic, butyric, isobutyric, valeric and pivalic; acyl groups from aromatic or heteroaromatic carboxylic acids derive from benzoic or pyridinecarboxylic (2-, 3- or 4-pyridinecarboxylic), pyrrolecarboxylic, isoxazolecarboxylic and quinolinecarboxylic acid optionally substituted by alkyl, alkoxy, halogen or nitro groups.

Specific examples comprise benzoyl, 2-pyridinecarbonyl, 3-pyridinecarbonyl, 4-pyridinecarbonyl, 2-chlorobenzoyl, 4-chlorobenzoyl, 2-methylbenzoyl, 3-methylbenzoyl, 4-methylbenzoyl, 2,4-dimethylbenzoyl, 4-nitrobenzoyl, 4-isobutylbenzoyl, 4-methoxybenzoyl, 2-methoxybenzoyl, 3-methoxybenzoyl.

Preferred substituents for carbamic and carbonic acids are alkyl and phenyl.

The halogen atoms are fluorine, chlorine, bromine and iodine. Preferred compounds of formula I are the compounds in which the carbon atom marked by the asterisk has (S) configuration.

More preferred compounds of formula I are the compounds wherein R is OY, R$_1$ is OY', Y, Y' and R$_2$ are hydrogen atoms, n is an integer selected among 5, 6 and 7.

A class of still more preferred compounds of formula I are the compounds wherein R is OY, R$_1$ is OY', Y, Y' and R$_2$ are hydrogen atoms, n is 6, m is 1, p is 2 or 3, X is S, CO or NH, R$_4$ is phenyl optionally substituted by one or two methyl, methoxy, chloro groups. Another class of still more preferred compounds of formula I are the compounds wherein R is OY, R$_1$ is OY', Y, Y' and R$_2$ are hydrogen atoms, n is 6, m is 1, p is 2, X is S, O or a single bond, R$_4$ is an heteroaryl selected among thienyl, pyridyl, imidazolyl and isoxazolyl, optionally substituted by a hydroxy, methyl or methoxy group.

Specific examples of preferred compounds of formula I are:

(S)-N-propyl-N-[6-[2-(2-methoxyphenylthio)ethylamino]hexyl]-5,6-dihydroxy-1,2,3,4-tetrahydro-2-naphthylamine (S)-N-propyl-N-[6-[2-(2,6-dichlorophenylthio)ethylamino]hexyl]-5,6-dihydroxy-1,2,3,4-tetrahydro-2-naphthylamine (S)-N-[2-(5,6-dihydroxy-1,2,3,4-tetrahydro)naphthyl]-N-propyl-N'-[2-(2-methoxyphenylthio)ethyl]-N'-propyl-1,6-hexanediamine (S)-N-[2-(5,6-dihydroxy-1,2,3,4-tetrahydro)naphthyl]-N-propyl-N'-[2-(2-methoxyphenylthio)ethyl]-N'-methyl-1,6-hexanediamine (S)-N-propyl-N-[6-[2-(2-chlorophenylthio)ethylamino]hexyl]-5,6-dihydroxy- 1,2,3,4-tetrahydro-2-naphthylamine (S)-N-propyl-N-[6-[3-(2-methoxyphenylthio)propylamino]hexyl]-5,6-dihydroxy-1,2,3,4-tetrahydro-2-naphthylamine (S)-N-propyl-N-[6-[3-(2,6-dichlorophenylthio)
propylamino]hexyl]-5,6-dihydroxy-1,2,3,4-tetrahydro-2-
naphthylamine (S)-N-propyl-N-[6-[4-(2-methoxyphenyl)-4-
oxobutylamino]hexyl]-5,6-dihydroxy-1,2,3,4-tetrahydro-
2-naphthylamine (S)-N-propyl-N-[6-[2-[(2-chloro-6-methylphenyl)thio]
ethylamino]hexyl]-5,6-dihydroxy-1,2,3,4-tetrahydro-2-
naphtylamine (S)-N-propyl-N-[6-[2-(2-thienyl)ethylamino]hexyl]-5,6-
dihydroxy-1,2,3,4-tetrahydro-2-naphthylamine (S)-N-propyl-N-[6-[2-(3-thienyl)ethylamino]hexyl]-5,6-
dihydroxy-1,2,3,4-tetrahydro-2-naphthylamine (S)-N-propyl-N-[6-[2-[(1-methyl-2-imidazolyl)thio]
ethylamino]hexyl]-5,6-dihydroxy-1,2,3,4-tetrahydro-2-
naphthylamine (S)-N-propyl-N-[6-[2-(4-imidazolyl)ethylamino]hexyl]-5,
6-dihydroxy-1,2,3,4-tetrahydro-2-naphthylamine (S)-N-propyl-N-[6-[3-(2-methoxyphenyl)-3-
oxopropylamino]hexyl]-5,6-dihydroxy-1,2,3,4-
tetrahydro-2-naphthylamine (S)-N-propyl-N-[6-[2-(3-methoxy-2-pyridyloxy)
ethylamino]hexyl]-5,6-dihydroxy-1,2,3,4-tetrahydro-2-
naphthylamine (S)-N-propyl-N-[6-[2-(4-pyridylthio)ethylamino]hexyl]-5,
6-dihydroxy-1,2,3,4-tetrahydro-2-naphthylamine (S)-N-propyl-N-[6-[2-(3-hydroxy-isoxazol-5-yl)
ethylamino]hexyl]-5,6-dihydroxy-1,2,3,4-tetrahydro-2-
naphthylamine (S)-N-propyl-N-[6-[2-(2-methoxyphenylamino)ethylamino]
hexyl]-5,6-dihydroxy-1,2,3,4-tetrahydro-2-
naphthylamine (S)-N-propyl-N-[6-[3-(2-methoxyphenylamino)
propylamino]hexyl]-5,6-dihydroxy-1,2,3,4-tetrahydro-2-
naphthylamine According to what is commonly known in the field of cathecol or phenol derivatives, the compounds of formula I wherein at least one of Y, Y' and Y" is different from hydrogen are prodrugs of the corresponding compounds of formula I.

Among the compounds of formula I, preferred prodrugs are the compounds wherein one or two of Y, Y' and Y", the same or different, are acyl groups deriving from acetic, propionic, butyric, isobutyric acid, from optionally substituted benzoic or pyridinecarboxylic acid, from phosphoric, carbamic or carbonic acid.

Still more preferred prodrugs are the compounds of formula I wherein two of Y, Y' and Y" are acyl groups deriving from acetic acid and the compounds of formula I wherein one or two of Y, Y' and Y" are acyl groups deriving from phosphoric acid.

Pharmaceutically acceptable salts of the compounds of formula I are the salts with organic or inorganic acids such as, for example, hydrochloric, hydrobromic, hydroiodic, nitric, sulphuric, phosphoric, acetic, benzoic, maleic, fumaric, succinic, tartaric, citric, aspartic, methansulphonic, 3,7-di-ter.butylnaphthalen-1,5-disulphonic (dibudinic acid) acid. Preferred salts of the compounds of formula I are the salts with hydrochloric or hydrobromic acid.

The preparation of the compounds of formula I can be carried out according to the synthetic method hereinafter described.

The method comprises the reaction between a compound of formula

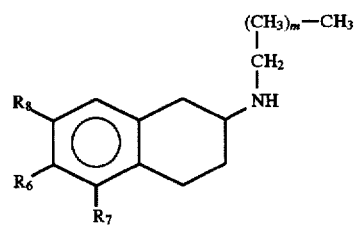

wherein
$R_6$ is a hydrogen atom or an $OY'''$ group wherein $Y'''$ is a hydrogen atom or a protecting group selected, for example, among methyl, benzyl, benzoyl and 4-methoxy-benzoyl;

$R_7$ and $R_8$, the same or different, are a hydrogen atom or an $OY'''$ group; provided that at least one of $R_6$, $R_7$ and $R_9$ is hydrogen but $R_6$, $R_7$ and $R_8$ are not contemporaneously hydrogen atoms and $R_7$ and $R_9$ are not contemporaneously $OY'''$ groups;

m has the already reported meanings;
and an acid of formula

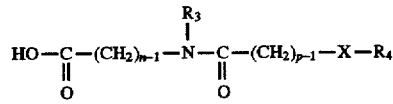

wherein n, p, X, $R_3$ and $R_4$ have the already reported meanings;

or a reactive derivative thereof such as an acyl halide or a mixed anhydride which can optionally be prepared in situ, in an inert solvent and in the presence of a base such as an alkali carbonate or bicarbonate or a tertiary amine, in order to obtain the intermediate compounds of formula

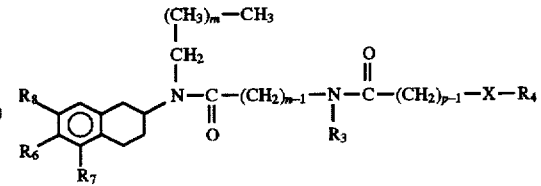

wherein m, n, p, X, $R_3$, $R_4$, $R_6$, $R_7$ and $R_8$ have the already reported meanings;

and their reduction, preceded or followed by the optional deprotection of the hydroxy groups, to obtain the compounds of formula I.

The reduction of the compounds of formula IV can be carried out with electrophilic reducing agents, in particular with diborane optionally complexed with dimethylsulphide, tetrahydrofuran, aliphatic amines such as triethylamine or aromatic amines such as N,N-diethyl-aniline or pyridine.

Alternatively, the reduction can be carried out with nucleophilic reducing agents such as metal hydrides, for example lithium aluminum hydride.

The reduction reaction is carried out in a suitable solvent such as for example tetrahydrofuran, diethylether or 1,2-dimethoxyethane. The optional deprotection of the hydroxy groups is carried out according to conventional techniques such as hydrolysis or hydrogenolysis.

The compounds of formula I wherein $R_3$ is different from hydrogen can be also prepared by alkylation of the corresponding compounds of formula I wherein $R_3$ is hydrogen ($R_3$=H).

The alkylation can be carried out for example by treatment of the compounds of formula I ($R_3$=H) with a suitable $C_1$–$C_4$ aliphatic carboxylic acid or a reactive derivative thereof, followed by reduction of the resultant amide derivative.

The compounds of formula II are known or they are easy prepared according to known methods (British patent no. 1509454—The Wellcome Foundation Ltd.).

Also the compounds of formula III are known or they are easy prepared according to conventional methods such as the condensation between an amino acid of formula

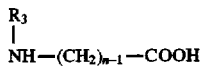

(V)

wherein $R_3$ and n have the already reported meanings; and an acid derivative of formula

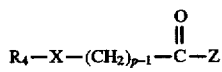

(VI)

wherein $R_4$, p and X have the already reported meanings and Z is a chlorine or bromine atom.

Alternatively, the synthesis of the compounds of formula I can be carried out through a different sequence.

Accordingly, the compounds of formula II can be reacted, first, with an amino acid of formula V, optionally protected on the amino function, or with a reactive derivative thereof to obtain the intermediate of formula

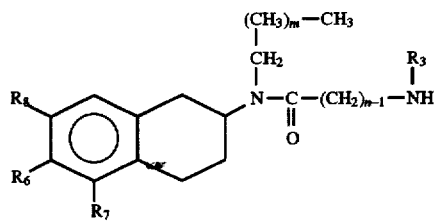

(VII)

wherein m, n, $R_3$, $R_4$, $R_7$ and $R_8$ have the already reported meanings; which is then reacted with a halide of formula

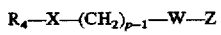

(VIII)

wherein p, X, $R_4$ and Z have the already reported meanings and W is a $CH_2$ or CO group;
or with an acid of formula

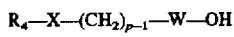

(VIII-A)

wherein p, X and $R_4$ have the already reported meanings and W is a CO group;
obtaining the corresponding intermediates of formula An alternative method for the preparation of the compounds of formula I, wherein X is a CO group, consists in a first reduction of a compound of formula VII, according to the already described reduction reaction, followed by the reaction of the so obtained intermediate of formula

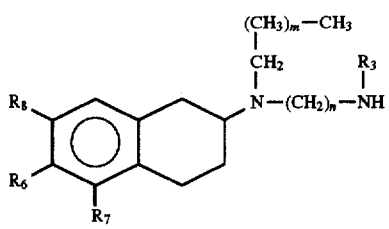

(X)

wherein m, n, $R_3$, $R_6$, $R_7$ and $R_8$ have the already reported meanings; with a compound of formula

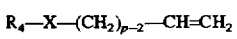

(XI)

wherein p and $R_4$ have the already reported meanings and X is a CO group;
obtaining the corresponding compound of formula I, after optional deprotection.

The intermediates of formula XI are known or easy prepared by known methods.

The compounds of formula I in optically active form are obtained by optical separat ion or by stereospecific or stereoselective syntheses.

The preparation of the salts of the compounds of formula I is carried out according to conventional methods.

The compounds of formula I are agonists of $D_1$ and $D_2$ dopaminergic receptors at least 10 times more potent than dopamine as shown by the in vitro binding tests (example 24).

Furthermore, they are also more potent than dopexamine as well as than the compounds described in the above cited European patent application No. 321968.

The compounds of formula I, object of the present invention, are also active in vivo after oral administration (example 25) contrary to dopamine and to dopexamine.

Moreover, specific interaction tests have shown that the compounds of formula I do not significantly interact with other receptor systems and thus they are endowed with very high specificity.

The compounds of formula I also show to be inactive on the central nervous system by oral administration and this lack of effect is a further positive property which is not shared by other compounds having a cathecolamine structure.

It is clear that these characteristics of selectivity and receptor specificity together with the lack of activity on the

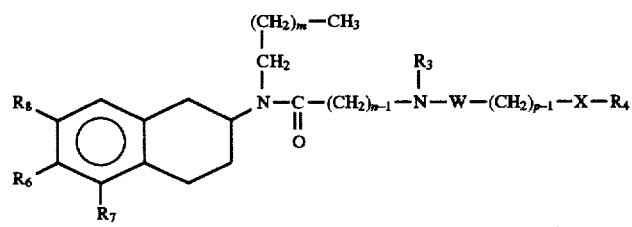

(IX)

wherein m, n, p, X, W, $R_3$, $R_4$, $R_6$, $R_7$ and $R_8$ have the already reported meanings.

The subsequent reduction, preceded or followed by the optional deprotection of the hydroxy groups, gives the compounds of formula I, object of the present invention.

The intermediates of formula VI, VIII and VIII-A are known or easy prepared according to conventional method.

central nervous system make the compounds of formula I particularly suitable for the treatment of cardiovascular diseases and mainly in the anti-hypertensive therapy, in the therapy of heart failure, of renal insufficiency, in the treatment of peripheral arteriopathies and in cerebrovascular insufficiencies.

In addition to the better activity, the selectivity and the receptor specificity, the further feature which makes different the compound of formula I, object of the invention, from the reference compounds is their adsorption by oral route and their long action.

Consequently, for the practical therapeutic uses, the compounds of formula I can be administered by infusion as well as by enteral route so differing from dopamine and from dopexamine.

The therapeutic doses will be generally between 5 mg and 1 g a day and between 5 and 300 mg by oral route for each administration.

The pharmaceutical compositions containing an effective therapeutic amount of one or more compounds of formula I or pharmaceutically acceptable salts thereof in admixture with a suitable carrier are a further object of the present invention.

The pharmaceutical compositions object of the invention can be liquid, suitable for enteral or parenteral administration, and preferably, solid such as tablets, capsules, granulates, suitable for oral administration.

The preparation of the pharmaceutical compositions object of the invention can be carried out according to traditional techniques.

In order to better illustrate the present invention the following examples are now given.

EXAMPLE 1

Preparation of (S)-N-propionyl-5,6-dimethoxy-1,2,3,4-tetrahydro-2-naphthylamine

Propionyl chloride (14.3 ml; 165 mmoles) was added to a solution of (S)-5,6-dimethoxy-1,2,3,4-tetrahydro-2-naphthylamine (31 g; 150 mmoles) and triethylamine (23 ml; 165 mmoles) in N,N-dimethylformamide (310 ml) at room temperature and under nitrogen. The reaction mixture was kept under stirring for 1 hour, then it was poured into water (1.5 l).

The solid was filtered by washing with water and dried at 50° C. under vacuum obtaining (S)-N-propionyl-5,6-dimethoxy-1,2,3,4-tetrahydro-2-naphthylamine (32.8 g). m.p. 149°–151° C.

$^1$H-NMR (300 MHz, CDCl$_3$): δ (ppm): 1.14 (t, 3H); 1.70–1.80 (m, 1H); 2.02 (m, 1H); 2.18 (q, 2H); 2.57 (dd, 1H); 2.75–3.00 (m, 2H); 3.04 (dd, 1H); 3.80 (s, 3H); 3.84 (s, 3H); 4.25 (m, 1H); 5.47 (bd, 1H); 6.74 (d, 1H); 6.78 (d, 1H).

Mass (chemical ionization, isobutane, positive ions): 264 [M+1], 190.

EXAMPLE 2

Preparation of (S)-N-propyl-5,6-dimethoxy-1,2,3,4-tetrahydro-2-naphthylamine hydrochloride Borane-dimethylsulphide complex (82 ml; 854.4 mmoles) was added dropwise, at room temperature and under nitrogen, to a solution of (S)-N-propionyl-5,6-dimethoxy-1,2,3,4-tetrahydro-2-naphthylamine (22.5 g; 85.4 mmoles), prepared as described in example 1, in anhydrous tetrahydrofuran (900 ml). The reaction mixture was heated under reflux for 1.5 hours. After cooling to 15° C., a 36% solution of hydrochloric acid (9.5 ml) in methanol (247 ml) was added dropwise with caution.

The mixture was heated under reflux for 1 hour, then the solvent (about 500 ml) was distilled off at atmospheric pressure and evaporated to dryness under vacuum.

The resultant crude was collected with absolute ethanol and the solution was heated under reflux obtaining, after cooling and filtration, (S)-N-propyl-5,6-dimethoxy-1,2,3,4-tetrahydro-2-naphthylamine hydrochloride (23 g). m.p. 257°–262° C.

$^1$H-NMR (300 MHz, DMSO-d$_6$): δ (ppm): 0.96 (t, 3H); 1.65–1.80 (m, 3H); 2.29 (m, 1H); 2.60 (m, 1H); 2.80–3.00 (m, 4H); 3.13 (dd, 1H); 3.34 (m, 1H); 3.68 (s, 3H); 3.77 (s, 3H); 6.83 (d, 1H); 6.89 (d, 1H).

Mass (chemical ionization, isobutane, positive ions): 250 [M+1].

EXAMPLE 3

Preparation of (S)-N-propyl-5,6-dihydroxy-1,2,3,4-tetrahydro-2-naphthylamine hydrobromide A solution of (S)-N-propyl-5,6-dimethoxy-1,2,3,4-tetrahydro-2-naphthylamine hydrochloride (22 g; 76.9 mmoles), prepared as described in example 2, in 48% hydrobromic acid (220 ml) was heated under reflux (about 130° C.) for 3 hours. The solvent was evaporated to dryness under vacuum and the residue was taken twice with toluene, by evaporating to dryness each time. The resultant crude was collected with ethyl acetate and filtered obtaining (S)-N-propyl-5,6-dihydroxy-1,2,3,4-tetrahydro-2-naphthylamine hydrobromide (23 g). m.p. 219°–222° C. [α]$_D$=−54.59° (1% in methanol)

$^1$H-NMR (300 MHz, DMSO-d$_6$): δ (ppm): 0.93 (t, 3H); 1.68 (m, 3H); 2.25 (m, 1H); 2.40–2.55 (m, 1H); 2.70–3.10 (m, 5H); 3.31 (m, 1H); 6.40 (d, 1H); 6.61 (d, 1H).

Mass (chemical ionization, isobutane, positive ions): 222 [M+1].

EXAMPLE 4

Preparation of [(1-methyl-2-imidazolyl)thio]acetic acid ethyl ester

A solution of 2-mercapto-1-methylimidazole (5.7 g; 50.0 mmoles) in N,N-dimethylformamide (10 ml) was added dropwise to a suspension of sodium hydride (1.3 g; 54.1 mmoles) in N,N-dimethylformamide (40 ml), kept under stirring at room temperature, while checking that the temperature does not exceed 35° C.

After 45 minutes, ethyl bromoacetate (8.4 g; 50.0 mmoles) was added.

The reaction mixture was kept under stirring at room temperature for 2 hours.

After addition of water (100 ml) and ethyl ether (150 ml), the phases were separated and the organic phase was dried on anhydrous sodium sulphate and evaporated to dryness.

The resultant crude was purified by column chromatography on silica gel (230–400 mesh), eluent methylene chloride:methanol=99:1, obtaining [(1-methyl-2-imidazolyl)thio]acetic acid ethyl ester (3.4 g) as an oil.

$^1$H-NMR (200 MHz, CDCl$_3$): δ (ppm): 1.20 (t, 3H); 3.64 (s, 3H); 3.78 (s, 2H); 4.12 (q, 2H); 6.89 (d, 1H); 7.02 (d, 4H).

Mass (chemical ionization, isobutane, positive ions): 201 [M+1].

By working in a similar way, the following compounds were prepared:

(2-methoxyphenylthio)acetic acid ethyl ester $^1$H-NMR (200 MHz, CDCl$_3$): δ (ppm): 1.17 (t, 3H); 3.60 (s, 3H); 3.88 (s, 3H); 4.11 (q, 2H); 6.81–7.39 (m, 4H).

Mass (chemical ionization, isobutane, positive ions): 227 [M+1].

3-(2-methoxyphenylthio)propionic acid ethyl ester

¹H-NMR (200 MHz, CDCl₃): δ (ppm): 1.22 (t, 3H); 2.58 (t, 2H); 3.11 (t, 2H); 3.87 (s, 3H); 4.11 (q, 2H); 6.81–7.32 (m, 4H).

Mass (chemical ionization, isobutane, positive ions): 241 [M+1].

(2,6-dichlorophenylthio)acetic acid ethyl ester

¹H-NMR (200 MHz, CDCl₃): δ (ppm): 1.15 (t, 3H); 3.56 (s, 2H); 4.07 (q, 2H); 7.18–7.39 (m, 3H).

Mass (chemical ionization, isobutane, positive ions): 265 [M+1].

EXAMPLE 5

Preparation of [(1-methyl-2-imidazolyl)thio]acetic acid hydrochlride

A solution of [(1-methyl-2-imidazolyl)thio]acetic acid ethyl ester (2.80 g; 14.0 mmoles), prepared as described in example 4, in dioxane (30 ml) and concentrated hydrochloric acid (40 ml) was kept under stirring and under reflux for 3 hours.

The solvents were evaporated under reduced pressure and the resultant residue was collected with toluene.

The solvent was evaporated under reduced pressure, the residue was collected with toluene again and then with methylene chloride by evaporating the solvent each time.

The resultant solid was triturated in methylene chloride and filtered obtaining [(1-methyl-2-imidazolyl)thio]acetic acid (2.74 g) as a white solid.

¹H-NMR (200 MHz, DMSO-d₆): δ (ppm): 3.81 (s, 3H); 4.20 (s, 2H); 7.73 (d, 1H); 7.81 (d, 1H).

Mass (chemical ionization, isobutane, positive ions): 173 [M+1].

EXAMPLE 6

Preparation of (3-methoxy-2-pyridyloxy)acetic acid ethyl ester

Silver carbonate (8.3 g; 30.0 mmoles) and ethyl bromoacetate (26.7 g; 160.0 mmoles) were added to a suspension of 3-methoxy-1,2-dihydro-pyridin-2(1H)-one (5.0 g; 40.0 mmoles) in toluene (80 ml).

The reaction mixture was heated under reflux, under stirring and in the dark, for 30 hours.

After cooling at room temperature, the reaction mixture was filtered, the resultant solution was washed with an 1% aqueous sodium bicarbonate solution and then with water.

The organic solution was dried on anhydrous sodium sulphate and the solvent evaporated under reduced pressure.

The resultant residue was purified by column chromatography on silica gel (230–400 mesh), eluent methylene chloride, obtaining (3-methoxy-2-pyridyloxy)acetic acid ethyl ester (3.8 g) as a solid.

¹H-NMR (200 MHz, CDCl₃): δ (ppm): 1.21 (t, 3H); 3.86 (s, 3H); 4.20 (q, 2H); 4.93 (s, 2H); 6.80–7.65 (m, 3H).

Mass (chemical ionization, isobutane, positive ions): 212 [M+1].

EXAMPLE 7

Preparation of (3-methoxy-2-pyridyloxy)acetic acid hydrochloride

A solution of sodium hydroxide (1.9 g; 47.5 mmoles) in water (10 ml) was added dropwise to a solution of (3-methoxy-2-pyridyloxy)acetic acid ethyl ester (3.7 g; 17.5 mmoles), prepared as described in example 6, in methanol (40 ml), under stirring at room temperature. The reaction mixture was kept under stirring for 3.5 hours.

The solvents were evaporated under reduced pressure and the resultant residue was dissolved in water (70 ml).

By acidification with concentrated hydrochloric acid up to pH 1, a precipitate was obtained, filtered, washed with water and then with petroleum ether.

After drying under vacuum at 40° C., (3-methoxy-2-pyridyloxy)acetic acid hydrochloride (2.9 g) was obtained as a white solid.

¹H-NMR (200 MHz, DMSO-d₆): δ (ppm): 3.79 (s, 3H); 4.80 (s, 2H); 6.90–7.65 (m, 3H); 12.78 (bs, 1H).

Mass (chemical ionization, isobutane, positive ions): 184 [M+1].

By working in a similar way, the following compounds were prepared:

(2-methoxyphenylthio)acetic acid

¹H-NMR (200 MHz, CDCl₃): δ (ppm): 3.62 (s, 2H); 3.86 (s, 3H); 6.83–7.41 (m, 4H).

Mass (chemical ionization, isobutane, positive ions): 199 [M+1].

3-(2-methoxyphenylthio)propionic acid

¹H-NMR (200 MHz, CDCl₃): δ (ppm): 2.64 (t, 2H); 3.11 (t, 3H); 3.88 (s, 3H); 6.83–7.34 (m, 4H).

Mass (chemical ionization, isobutane, positive ions): 213 [M+1].

(2,6-dichlorophenylthio)acetic acid

¹H-NMR (200 MHz, CDCl₃): δ (ppm): 3.46 (s, 2H); 6.10–6.60 (bs, 1H); 7.03–7.28 (m, 3H).

Mass (chemical ionization, isobutane, positive ions): 237 [M+1].

EXAMPLE 8

Preparation of 6-[(2-methoxyphenylthio) acetylamino]hexanoic acid a) Thionyl chloride (5.4 g; 45.4 mmoles) was added to a solution of (2-methoxyphenylthio)acetic acid (6.0 g; 30.3 mmoles), prepared as described in example 7, in methylene chloride (45 ml), under stirring at room temperature.

After 1 hour the solvent was evaporated under reduced pressure obtaining (2-methoxyphenylthio)acetyl chloride (6.54 g; 30.2 mmoles) as an oil which was dissolved in methylene chloride (8 ml).

b) A solution of (2-methoxyphenylthio)acetyl chloride, prepared as described in point a, and a 4N solution of sodium hydroxide (8 ml) were contemporaneously added dropwise under vigorous stirring to a solution of 6-aminohexanoic acid (3.3 g; 25.7 mmoles) and sodium hydroxide (1.03 g; 25.7 mmoles) in water (9 ml).

The reaction mixture was kept under stirring at room temperature for 4 hours.

The phases were separated and the aqueous phase was washed with methylene chloride (10 ml), acidified with 37% hydrochloric acid up to pH 1 and extracted with methylene chloride (15 ml). The resultant organic phase was dried on anhydrous sodium sulphate and the solvent was evaporated under reduced pressure obtaining a crude residue.

The crude was purified by column chromatography on silica gel (230–400 mesh), eluent methylene chloride:methanol:glacial acetic acid=95:5:0.5, obtaining 6-[(2-methoxyphenylthio)acetylaminolhexanoic acid (7.7 g) as a white solid. m.p. 85°–87° C.

¹H-NMR (300 MHz, CDCl₃): δ (ppm): 1.20 (m, 2H); 1.32–1.62 (m, 4H); 2.24 (t, 2H); 3.20 (m, 2H); 3.61 (s, 2H); 3.88 (s, 3H); 6.81–7.24 (m, 4H); 7.01 (bt, 1H);

Mass (chemical ionization, isobutane, positive ions): 312 [M+1].

By working in a similar way, the following compounds were prepared:
6-[(2,6-dichlorophenylthio)acetylamino]hexanoic acid m.p. 91°–92° C.

$^1$H-NMR (300 MHz, CDCl$_3$): δ (ppm): 1.20–1.36 (m, 2H); 1.41–1.68 (m, 4H); 2.29 (t, 2H); 3.21 (m, 2H); 3.69 (s, 2H); 7.14 (bt, 1H); 7.17–7.41 (m, 3H).

Mass (chemical ionization, isobutane, positive ions): 350 [M+1].

6-[3-(2-methoxyphenylthio)propionylamino]hexanoic acid $^1$H-NMR (300 MHz, CDCl$_3$): δ (ppm): 1.22–1.69 (m, 6H); 2.31 (t, 2H); 2.43 (t, 2H); 3.13 (t, 2H); 3.22 (m, 2H); 3.85 (s, 3H); 6.01 (bt, 1H); 6.80–7.31 (m, 4H).

Mass (chemical ionization, isobutane, positive ions): 326 [M+1].

EXAMPLE 9

Preparation of 2-(2-methoxyphenylamino)-2-oxo-ethylamine hydrochloride

37% Hydrochloric acid (4.2 ml) and 10% palladium on charcoal (50% in water, 1.4 g) were added to a solution of 2-benzyloxycarbonylamino-N-(2-methoxyphenyl) acetamide (14.2 g; 45.2 mmoles) in methanol (500 ml).

The reaction mixture was hydrogenated in a Parr apparatus (2.7 atm) at room temperature for 1 hour.

The catalyst was filtered off and the solvent was evaporated under reduced pressure.

The resultant solid crude was purified by crystallization from a mixture ethanol-isopropanol, obtaining 2-(2-methoxyphenylamino)-2-oxo-ethylamine hydrochloride (7.9 g) as a white solid.

$^1$H-NMR (200 MHz, DMSO$_6$): δ (ppm): 3.33 (s, 2H); 3.82 (s, 3H); 6.87–7.99 (m, 4H); 8.28 (bs, 3H); 9.76 (bs, 1H).

Mass (thermospray): 181 [M+1].

EXAMPLE 10

Preparation of 7-[2-(2-methoxyphenylamino)-2-oxo-ethylaminol-7-oxo-eptanoic acid A solution of eptandioic acid monomethyl ester chloride (6.4 g; 33.2 mmoles) in methylene chloride (10 ml) was added to a solution of triethylamine (9.6 g; 95.0 mmoles) and 2-(2-methoxyphenylamino)-2-oxo-ethylamine hydrochloride (6.8 g; 31.3 mmoles) in methylene chloride (90 ml), under stirring at room temperature.

After 2 hours, water (100 ml) was added and the phases were separated.

The organic phase was washed with an 1N aqueous HCl solution and then with a 10% aqueous sodium bicarbonate solution.

After drying on anhydrous sodium sulphate and evaporation to dryness under reduced pressure, the resultant residue was dissolved in methanol (20 ml).

A solution of sodium hydroxide (4.0 g; 100.0 mmoles) in water (10 ml) was added dropwise to the resultant solution, under stirring at room temperature.

The reaction mixture was kept under stirring for 1.5 hours.

The solvents were evaporated under reduced pressure and the residue was dissolved in water (30 ml).

The solution was washed with ethyl ether (30 ml), acidified with 37% hydrochloric acid up to pH 1 and extracted with ethyl acetate.

The resultant organic solution was brought to dryness under reduced pressure.

After drying at 50° C. under vacuum for 6 hours, 7-[2-(2-methoxyphenylamino)-2-oxo-ethylamino]-7-oxo-eptanoic acid (7.8 g) was obtained as a white solid.

$^1$H-NMR (200 MHz, DMSO-d$_6$): δ (ppm): 1.16–1.62 (m, 6); 2.09–2.24 (m, 4H); 3.82 (s, 3H); 3.87 and 3.90 (2d, 2H); 6.85–8.07 (m, 4H); 8.30 (t, 1H); 9.02 (s, 1H); 11.99 (bs, 1H).

EXAMPLE 11

Preparation of (S)-N-propyl-N-[6-[2-(2-methoxyphenylthio)ethylamino]hexyl]-5,6-dihydroxy-1,2,3,4-tetrahydro-2-naphthylamine dihydrochloride (Compound 1)

a) Thionyl chloride (2.06 g; 17.3 mmoles) was added to a solution of 6-[(2-methoxyphenylthio)acetylamino] hexanoic acid (2.05 g; 6.5 mmoles), prepared as described in example 8, in methylene chloride (13 ml). After 1.5 hours at room temperature, the reaction mixture was evaporated to dryness under reduced pressure. A yellow crude oil which was used as such in the subsequent reaction was obtained.

b) Sodium tetraborate (2.01 g; 10.0 mmoles) was added under nitrogen to a solution of (S)-N-propyl-5,6-dihydroxy-1,2,3,4-tetrahydro-2-naphthylamine hydrobromide (1.51 g; 5.0 mmoles) prepared as described in example 3, in water (30 ml).

The mixture was heated at 70° C. up to complete dissolution.

After cooling at room temperature, methylene chloride (3 ml), potassium carbonate (5.40 g; 39.1 mmoles) and, under vigorous stirring, a solution of the acyl chloride, prepared as described in point a, in methylene chloride (6 ml) were added. After 1 hour at room temperature, the reaction mixture was acidified with 37% hydrochloric acid up to pH 1 and the phases were separated.

The aqueous phase was extracted with methylene chloride (15 ml).

The two organic phases were collected, washed with brine slightly acidified with hydrochloric acid and then dried on anhydrous sodium sulphate.

After filtration and evaporation to dryness, a solid residue was obtained and dissolved under nitrogen in tetrahydrofuran (18 ml). Borane-dimethylsulphide complex (3.60 g; 46.7 mmoles) was slowly added to the resultant solution under stirring. At the end of the addition, the reaction mixture was heated under reflux for 2 hours. After cooling at 10° C., a 37% solution of hydrochloric acid (2.2 ml) in methanol (20 ml) was added. The reaction mixture was heated again under reflux for 1 hour, then concentrated by distilling the solvents at atmospheric pressure and brought to dryness under reduced pressure. The resultant residue was dissolved in methanol (25 ml); the solvent was distilled off under reduced pressure, methanol (25 ml) was added and the solvent was distilled off again to dryness. Then, the residue was dissolved in absolute ethanol (25 ml) and a 15% (w/v) solution of hydrochloric acid in ethyl ether (0.5 ml) was added.

After evaporation of the solvents, a residue which was purified by column chromatography on silica gel (230–400 mesh), eluent methylene chloride:methanol: 50% formic acid=85:15:2, was obtained. The resultant solid was dissolved in absolute ethanol (25 ml). A 15% (w/v) solution of hydrochloric acid in ethyl ether was added up to clearly acid pH and the solvents were evaporated under reduced pressure.

Compound 1 (0.86 g) was obtained as a white amorphous solid.

$^1$H-NMR (300 MHz, D$_2$O): δ (ppm): 0.78 (t, 3H); 1.12–2.16 (m, 12H); 2.34–3.55 (m, 15H); 3.70 (s, 3H); 6.46 (d, 1H); 6.59 (d, 1H); 6.79–7.31 (m, 4H).

Mass (chemical ionization, isobutane, positive ions): 487 [M+1].

By working in a similar way, the following compounds were prepared:

(S)-N-propyl-N-[6-[2-(2,6-dichlorophenylthio)ethylamino]hexyl]-5,6-dihydroxy-1,2,3,4-tetrahydro-2-naphthylamine dihydrochloride (Compound 2)

$^1$H-NMR (300 MHz, D$_2$O): δ (ppm): 0.80 (t, 3H); 1.18–2.19 (m, 12H); 2.38–3.11 (m, 14H); 3.46–3.61 (m, 1H); 6.47 (d, 1H); 6.58 (d, 1H); 7.13–7.36 (m, 3H).

Mass (chemical ionization, isobutane, positive ions): 525 [M+1].

(S)-N-propyl-N-[6-[3-(2-methoxyphenylthio)propylamino]hexyl]-5,6-dihydroxy-1,2,3,4-tetrahydro-2-naphthylamine dihydrochloride (Compound 3)

$^1$H-NMR (200 MHz, D$_2$O): δ (ppm): 0.79 (t, 3H); 1.15–2.17 (m, 14H); 2.36–3.10 (m, 14H); 3.41–3.57 (m, 1H); 3.70 (s, 5H); 6.47 (d, 1H); 6.60 (d, 1H); 6.81–7.26 (m, 4H).

Mass (chemical ionization, isobutane, positive ions): 501 [M+1].

(S)-N-propyl-N-[7-[2-(2-methoxyphenylamino)ethylamino]eptyl]-5,6-dihydroxy-1,2,3,4-tetrahydro-2-naphthylamine trihydrochloride (Compound 4)

$^1$H-NMR (200 MHz, D$_2$O): δ (ppm): 0.83 (t, 3H); 1.18–2.20 (m, 14H); 2.41–3.20 (m, 12H); 3.43–3.60 (m, 3H); 3.75 (s, 3H); 6.52 (d, 1H); 6.65 (d, 1H); 6.87–6.98 (m, 4H).

Mass (chemical ionization, isobutane, positive ions): 484 [M+1].

EXAMPLE 12

Preparation of (S)-N-[2-(5,6-dihydroxy-1,2,3,4-tetrahydro)naphthyl]-N-propyl-N'-[2-(2-methoxyphenylthio)ethyl]-N'-propyl-1,6-hexanediamine dihydrochloride (Compound 5)

Water (20 ml) and potassium carbonate (4.5 g; 32.5 mmoles) were fast added to a suspension of (S)-N-propyl-N-[6-[2-(2-methoxyphenylthio)-ethylamino]hexyl]-5,6-dihydroxy-1,2,3,4-tetrahydro-2-naphthylamine dihydrochloride (4.5 g; 8.0 mmoles), prepared as described in example 11, in methylene chloride (200 ml) under nitrogen and then a solution of propionyl chloride (0.8 g; 8.8 mmoles) in toluene (5 ml) was added under vigorous stirring.

The reaction mixture was kept under stirring at room temperature for 1 hour. The phases were separated and the organic phase was washed with brine slightly acidified with hydrochloric acid, then dried on anhydrous sodium sulphate and evaporated to dryness under reduced pressure. The resultant residue was dissolved in tetrahydrofuran (200 ml).

Borane-dimethylsulphide complex (3.7 g; 48.0 mmoles) was slowly added to the resultant solution, under stirring and under nitrogen. At the end of the addition, the reaction mixture was heated under reflux for 2 hours. After cooling at 5° C., a solution of 37% hydrochloric acid (2.5 ml) in methanol (16 ml) was added and the reaction mixture was heated again under reflux for 2.5 hours, then concentrated by distilling off the solvents at atmospheric pressure and brought to dryness under reduced pressure.

The resultant residue was dissolved in methanol (50 ml); the solvent was distilled off under reduced pressure, methanol was added (50 ml) and the solvent was distilled again up to dryness.

Then, the crude was dissolved in absolute ethanol (50 ml) and a 15% (w/v) solution of hydrochloric acid in ethyl ether was added up to complete acidification.

After evaporation of the solvents, a residue was obtained and purified by column chromatography on silica gel (230–400 mesh), eluent methylene chloride:methanol: 50% formic acid=90:10:2.

The resultant solid was dissolved in absolute ethanol (50 ml), treated with a 15% (w/v) solution of hydrochloric acid in ethyl ether up to clearly acid pH; the solvents were evaporated under reduced pressure.

Compound 5 (1.8 g) was obtained as a white amorphous solid.

$^1$H-NMR (300 MHz, D$_2$O) ): δ (ppm): 0.73 (t, 3H); 0.80 (t, 3H); 1.09–2.19 (m, 14H); 2.37–3.10 (m, 16 H); 3.40–3.57 (m, 1H); 3.71 (s, 3H); 6.48 (d, 1H); 6.61 (d, 1H); 6.80–7.33 (m, 4H).

Mass (chemical ionization, isobutane, positive ions): 529 [M+1].

By working in a similar way, the following compound was prepared:

(S)-N-[2-(5,6-dihydroxy-1,2,3,4-tetrahydro)naphthyl]-N-propyl-N'-[2-(2-methoxyphenylthio)ethyl]-N'-methyl-1,6-hexanediamine dihydrochloride (Compound 6)

$^1$H-NMR (200 MHz, D$_2$O) ): δ (ppm): 0.82 (t, 3H); 1.16–2.18 (m, 12H); 2.69 (s, 3H); 2.33–3.16 (m, 14H); 3.40–3.56 (m, 1H); 3.72 (s, 3H); 6.49 (d, 1H); 6.62 (d, 1H).

Mass (chemical ionization, isobutane, positive ions): 501 [M+1].

EXAMPLE 13

Preparation of (S)-N-propyl-N-[(6-phthalimido-1-oxo)hexyl]-5,6-dimethoxy-1,2,3,4-tetrahydro-2-naphthylamine Triethylamine (12.7 g; 126.1 mmoles) and then a solution of 6-phthalimidohexanoic acid chloride (15.5 g; 55.5 mmoles) in methylene chloride (120 ml) were added to a suspension of (S)-N-propyl- 5,6-dimethoxy-1,2,3,4-tetrahydro-2-naphthylamine hydrochloride (14.4 g; 50.4 mmoles), prepared as described in example 2, in methylene chloride (150 ml) kept under stirring at room temperature.

The reaction mixture was kept under stirring at room temperature for 1.5 hours.

After addition of water (250 ml), the phases were separated.

The organic phase was washed with water (150 ml), dried on anhydrous sodium sulphate and the solvent evaporated under reduced pressure.

The resultant residue was purified by column chromatography on silica gel (230–400 mesh), eluent petroleum ether-:ethyl acetate=6:4.

(S)-N-propyl-N-[(6-phthalimido-1-oxo)hexyl]-5,6-dimethoxy-1,2,3,4-tetrahydro-2-naphthylamine (24.1 g) was obtained.

$^1$H-NMR (200 MHz, CDCl$_3$): δ (ppm): 0.80–0.94 (2t, 3H); 1.30–2.02 (m, 10H); 2.26–2.38 (m, 2H); 2.59–3.22 (m, 6H); 3.60–3.72 (m, 2H); 3.75–3.84 (4s, 6H); 3.85–4.66 (m, 1H); 6.66–6.82 (m, 2H); 7.64–7.85 (m, 4H).

Mass (chemical ionization, isobutane, positive ions): 493 [M+1].

EXAMPLE 14

Preparation of (S)-N-[(6-amino-1-oxo)hexyl]-N-propyl-5,6-dimethoxy-1,2,3,4-tetrahydro-2-naphthylamine A solution of (S)-N-propyl-N-[(6-phthalimido-1-oxo)hexyl]-5,6-dimethoxy-1,2,3,4-tetrahydro-2-naphthylamine (24.1 g; 48.9 mmoles), prepared as described in example 13, in a 33% solution of methylamine in ethanol (240 ml) was kept under stirring at room temperature for 20 hours.

The reaction mixture was evaporated to dryness under reduced pressure and the resultant residue was purified by column chromatography on silica gel (230–400 mesh), eluent methylene chloride:methanol:30% ammonia= 90:10:1.

(S)-N-[(6-amino-1-oxo)hexyl]-N-propyl-5,6-dimethoxy-1,2,3,4-tetrahydro-2-naphthylamine (11.9 g) was obtained as an oil.

$^1$H-NMR (200 MHz, CDCl$_3$): δ (ppm): 0.80–0.93 (2t, 3H); 1.20–2.04 (m, 10H); 2.25–2.48 (m, 2H); 2.58–3.21 (m, 8H); 3.72–3.81 (4s, 6H); 3.82–4.64 (m, 1H); 6.66–6.80 (m, 2H).

Mass (chemical ionization, isobutane, positive ions): 363 [M+1].

EXAMPLE 15

Preparation of (S)-N-propyl-N-[6-[2-(2-thienyl)ethylamino]hexyl]-5,6-dimethoxy-1,2,3,4-tetrahydro-2-naphthylamine dihydrochloride Triethylamine (0.83 g; 8.3 mmoles) and then a solution of (2-thienyl)acetyl chloride (1.16 g; 7.2 mmoles), prepared as described in example 8.a, in methylene chloride (10 ml) were added to a solution of (S)-N-[(6-amino-1-oxo)hexyl]-N-propyl-5,6-dimethoxy-1,2,3,4-tetrahydro-2-naphthylamine (2.0 g; 5.5 mmoles), prepared as described in example 14, in methylene chloride (20 ml), kept under stirring at room temperature.

The reaction mixture was kept under stirring at room temperature for 3 hours.

After addition of water (30 ml), the phases were separated.

The organic phase was dried on anhydrous sodium sulphate and the solvent was evaporated under reduced pressure.

The resultant residue was dissolved in tetrahydrofuran (15 ml). Borane-dimethylsulphide complex (2.6 g; 32.5 mmoles) was slowly added to the resultant solution at room temperature, under stirring and under nitrogen.

At the end of the addition, the reaction mixture was heated under reflux for 2 hours.

After cooling at 5° C., a solution of 37% hydrochloric acid (1 ml) in methanol (7.5 ml) was added.

The reaction mixture was heated again under reflux for 1 hour, then concentrated by distilling the solvents at atmospheric pressure and brought to dryness under reduced pressure.

The resultant residue was dissolved in methanol (30 ml); the solvent was distilled under reduced pressure, methanol (30 ml) was added and the solvent was distilled again to dryness.

The residue was dissolved in absolute ethanol (30 ml) and a 15% (w/v) solution of hydrochloric acid in ethyl ether (10 ml) was added.

After evaporation of the solvent, (S)-N-propyl-N-[6-[2-(2-thienyl)-ethylamino]hexyl]-5,6-dimethoxy-1,2,3,4-tetrahydro-2-naphthylamine dihydrochloride (1.8 g) was obtained as white solid.

$^1$H-NMR (200 MHz, D$_2$O) ): δ (ppm): 0.80 (t, 3H); 1.17–2.20 (m, 12H); 2.44–3.21 (m, 14H); 3.45–3.60 (m, 1H); 3.59 (s, 3H); 3.68 (s, 3H); 6.79–7.20 (m, 5H).

Mass (chemical ionization, isobutane, positive ions): 459 [M+1].

By working in a similar way, the following compounds were prepared:
(S)-N-propyl-N-[6-[2-(3-thienyl)ethylamino]hexyl]-5,6-dimethoxy-1,2,3,4-tetrahydro-2-naphthylamine dihydrochloride $^1$H-NMR (200 MHz, CDCl$_3$): δ (ppm): 0.80 (t, 3H); 1.16–2.21 (m, 12H); 2.43–3.20 (m, 14H); 3.45–3.62 (m, 1H); 3.59 (s, 3H); 3.69 (s, 3H); 6.80–7.30 (m, 5H).

Mass (chemical ionization, isobutane, positive ions): 459 [M+1].

(S)-N-propyl-N-[6-[2-(4-imidazolyl)ethylamino]hexyl]-5,6-dimethoxy-1,2,3,4-tetrahydro-2-naphthylamine dihydrochloride $^1$H-NMR (200 MHz, CDCl$_3$): δ (ppm): 0.85 (t, 3H); 1.20–2.08 (m, 12H); 2.38–3.11 (m, 15H); 3.77 (s, 3H); 3.81 (s, 3H); 6.71 (d, 1H); 6.76 (s, 1H); 6.79 (d, 1H); 7.49 (s, 1H).

Mass (chemical ionization, isobutane, positive ions): 443 [M+1].

EXAMPLE 16

Preparation of (S)-N-propyl-N-[6-[2-(2-thienyl)ethylamino]hexyl]-5,6-dihydroxy-1,2,3,4-tetrahydro-2-naphthylamine dihydrobromide (Compound 7)

A solution of (S)-N-propyl-N-[6-[2-(2-thienyl)ethylamino]hexyl]-5,6-dimethoxy-1,2,3,4-tetrahydro-2-naphthylamine dihydrochloride (1.8 g; 3.3 mmoles), prepared as described in example 15, in 48% hydrobromic acid (17 ml) was heated under reflux and under nitrogen for 6 hours.

The reaction mixture was brought to dryness under reduced pressure and absolute ethanol (30 ml) was added to the resultant residue.

After evaporation of the solvent, ethyl acetate (30 ml) was added and the solvent was evaporated again under reduced pressure.

The resultant crude was purified by column chromatography on silica gel (230–400 mesh), eluent methylene chloride:methanol: 50% formic acid=85:15:1.

Compound 7 (0.42 g) was obtained as a white amorphous solid.

$^1$H-NMR (200 MHz, D$_2$O) ): δ (ppm): 0.80 (t, 3H); 1.18–2.18 (m, 12H); 2.38–3.21 (m, 14H); 3.45–3.59 (m, 1H); 6.49 (d, 1H); 6.62 (d, 1H); 6.82–7.19 (m, 3H).

Mass (chemical ionization, isobutane, positive ions): 431 [M+1].

By working in a similar way, the following compounds were prepared:
(S)-N-propyl-N-[6-[2-(3-thienyl)ethylamino]hexyl]-5,6-dihydroxy-1,2,3,4-tetrahydro-2-naphthylamine dihydrobromide (Compound 8)

$^1$H-NMR (200 MHz, D$_2$O) ): δ (ppm): 0.81 (t, 3H); 1.23–2.19 (m, 12H); 2.41–3.19 (m, 14H); 3.46–3.61 (m, 1H); 6.51 (d, 1H); 6.64 (d, 1H); 6.90–7.32 (m, 3H).

Mass (chemical ionization, isobutane, positive ions): 431 [M+1].

(S)-N-Propyl-N-[6-[2-(4-imidazolyl)ethylamino]hexyl]-5,6-dihydroxy-1,2,3,4-tetrahydro-2-naphthylamine dihydrobromide (Compound 9)

$^1$H-NMR (200 MHz, D$_2$O) ): δ (ppm): 0.82 (t, 3H); 1.22–2.23 (m, 12H); 2.41–3.27 (m, 14H); 3.47–3.63 (m, 1H); 6.52 (d, 1H); 6.64 (d, 1H); 7.21 (d, 1H); 8.48 (d, 1H).

Mass (chemical ionization, isobutane, positive ions): 415 [M+1].

EXAMPLE 17

Preparation of (S)-N-[(6-amino)hexyl]-N-propyl-5,6-dimethoxy-1,2,3,4-tetrahydro-2-naphthylamine dihydrochloride Borane-dimethylsulphide complex (3.0 g; 37 mmoles) was slowly added at room temperature to a solution of (S)-N-[(6-amino-1-oxo)hexyl]-N-propyl-5,6-dimethoxy-1,2,3,4-tetrahydro-2-naphthylamine (2.3 g; 6.34 mmoles), prepared as described in example 14, in tetrahydrofuran (40 ml), under stirring and under nitrogen.

At the end of the addition, the reaction mixture was heated under reflux for 2 hours.

After cooling at 5° C., a solution of 37% hydrochloric acid (1.5 ml) in methanol (12 ml) was added.

The reaction mixture was heated again under reflux for 1 hour, concentrated by distilling the solvent at atmospheric pressure and brought to dryness under reduced pressure.

The resultant residue was dissolved in methanol (30 ml); the solvent was distilled under reduced pressure, methanol was added (30 ml) and the solvent was distilled again to dryness.

The resultant crude was purified by column chromatography on silica gel (230–400 mesh), eluent methylene chloride:methanol: 50% formic acid=85:15:1.

The resultant solid was dissolved in absolute ethanol.

A 15% (w/v) solution of hydrochloric acid in ethyl ether was added up to clearly acid pH and the solvents were evaporated under reduced pressure.

(S)-N-[(6-amino)hexyl]-N-propyl-5,6-dimethoxy-1,2,3,4-tetrahydro-2-naphthylamine dihydrochloride (1.9 g) was obtained as a white amorphous solid.

$^1$H-NMR (200 MHz, D$_2$O) ): δ (ppm): 0.80 (t, 3H); 1.19–1.32 (m, 4H); 1.40–2.20 (m, 8H); 2.44–3.17 (m, 10H); 3.46–3.63 (m, 1H); 3.59 (s, 3H); 3.68 (s, 3H); 6.76–6.85 (2d, 2H).

Mass (chemical ionization, isobutane, positive ions): 349 [M+1].

EXAMPLE 18

Preparation of (S)-N-[(6-amino)hexyl]-N-propyl-5,6-dihydroxy-1,2,3,4-tetrahydro-2-naphthylamine dihydrobromide A solution of (S)-N-[(6-amino)hexyl]-N-propyl-5,6-dimethoxy-1,2,3,4-tetrahydro-2-naphthylamine dihydrochloride (1.2 g; 2.87 mmoles), prepared as described in example 17, in 48% hydrobromic acid (10 ml) was heated under reflux and under nitrogen for 5 hours.

The reaction mixture was evaporated to dryness under reduced pressure and absolute ethanol (20 ml) was added to the resultant residue.

The solvent was evaporated, ethyl acetate (20 ml) was added and the solvent was evaporated again under reduced pressure.

The resultant crude was purified by crystallization from a mixture absolute ethanol:ethyl acetate.

(S)-N-[(6-amino)hexyl]-N-propyl-5,6-dihydroxy-1,2,3,4-tetrahydro-2-naphthylamine dihydrobromide (1.2 g) was obtained as a white solid.

$^1$H-NMR (200 MHz, D$_2$O) ): δ (ppm): 0.80 (t, 3H); 1.21–2.19 (m, 12H); 2.39–3.11 (m, 10H); 3.44–3.60 (m, 1H); 6.50 (d, 1H); 6.62 (d, 1H).

Mass (chemical ionization, isobutane, positive ions): 321 [M+1].

EXAMPLE 19

Preparation of (S)-N-propyl-N-[6-[3-(2-methoxyphenyl)-3-oxopropylamino]hexyl]- 5,6-dihydroxy-1,2,3,4-tetrahydro-2-naphthylamine dihydrobromide (Compound 10)

A solution of (S)-N-[(6-amino)hexyl]-N-propyl-5,6-dihydroxy-1,2,3,4-tetrahydro-2-naphthylamine dihydrobromide (1.04 g; 2.16 mmoles), prepared as described in example 18, and 1-(2-methoxyphenyl)-2-propen-1-one (0.35 g; 2.16 mmoles), prepared as described in J. Chem. Soc. Perkin Trans. 1, 471–9 (1981), in N,N-dimethylformamide (10 ml) was heated under reflux for 2 hours.

The reaction mixture was evaporated to dryness under reduced pressure.

The resultant crude was purified by column chromatography on silica gel (230–400 mesh), eluent methylene chloride:methanol: 50% formic acid=85:15:1.

Compound 10 (0.49 g) was obtained as a white amorphous solid.

$^1$H-NMR (200 MHz, D$_2$O) ): δ (ppm): 0.80 (t, 3H); 1.22–2.19 (m, 12H); 2.37–3.59 (m, 15H); 3.75 (s, 3H); 6.48 (d, 1H); 6.60 (d, 1H); 6.86–7.57 (m, 4H).

Mass (electronic impact): M/e 135, 163, 234, 320.

EXAMPLE 20

Preparation of (S)-N-t.butoxycarbonyl-N-propyl-5,6-di(phenylmethoxy)-1,2,3,4-tetrahydro-2-naphthylamine A solution of di-t.butyldicarbonate (14.5 g; 66.2 mmoles) in N,N-dimethylformamide (28 ml) was added under stirring to a solution of (S)-N-propyl-5,6-dihydroxy-1,2,3,4-tetrahydro-2-naphthylamine hydrobromide (20 g; 66 mmoles), prepared as described in example 3, and triethylamine (6.7 g; 66 mmoles) in N,N-dimethylformamide (160 ml), at room temperature and under nitrogen.

The reaction mixture was kept under stirring for 3 hours and then poured into a mixture of water, ice and ethyl ether.

After addition of 1N hydrochloric acid up to clearly acid pH, the phases were separated.

The organic phase was washed twice with water, dried on anhydrous sodium sulphate and the solvent was evaporated under reduced pressure.

The resultant residue was dissolved in N,N-dimethylformamide (250 ml).

Potassium carbonate (34.4 g; 248.9 mmoles) and benzyl bromide (26.6 g; 155.5 mmoles) were added to the resultant solution, under stirring and at room temperature.

The reaction mixture was heated at 60° C. for 7 hours, then kept under stirring at room temperature for 16 hours and poured into a mixture of water and ethyl ether.

The phases were separated; the organic phase was washed with water, dried on anhydrous sodium sulphate and the solvent was evaporated under reduced pressure.

The resultant residue was purified by column chromatography on silica gel (230–400 mesh), eluent petroleum ether-:ethyl acetate=93:7.

(S)-N-t.butoxycarbonyl-N-propyl-5,6-di(phenylmethoxy)-1,2,3,4-tetrahydro-2-naphthylamine (23 g) was obtained as an oil.

$^1$H-NMR (200 MHz, CDCl$_3$): δ (ppm): 0.86 (t, 3H); 1.46 (s, 9H); 1.49–1.98 (m, 4H); 2.52–3.16 (m, 6H); 3.80–4.32 (broad signal, 1H); 4.99 (s, 2H); 5.10 (s, 2H); 6.74 (d, 1H); 6.81 (d, 1H); 7.25–7.47 (m, 10H).

Mass (chemical ionization, isobutane, positive ions): 502 [M+1].

EXAMPLE 21

Preparation of (S)-N-propyl-5,6-di(phenylmethoxy)-1,2,3,4-tetrahydro-2-naphthylamine hydrochloride A 13% (w/v) solution of hydrochloric acid in ethyl acetate (250 ml) was added to a solution of (S)-N-t.butoxycarbonyl-N-propyl-5,6-di-(phenylmethoxy)-1,2,3,4-tetrahydro-2-naphthylamine (23 g; 45.8 mmoles), prepared as described in example 20, in ethyl acetate (100 ml), under stirring at room temperature.

After 30 minutes, the precipitate was filtered, washed with ethyl acetate and dried under vacuum at 50° C. for 10 hours.

(S)-N-propyl-5,6-di(phenylmethoxy)-1,2,3,4-tetrahydro-2-naphthylamine hydrochloride (16.4 g) was obtained as a white solid.

$^1$H-NMR (200 MHz, CDCl$_3$): δ (ppm): 0.87 (t, 3H); 1.71–2.54 (m, 4H); 2.28–3.23 (m, 7H); 4.85 (s, 2H); 4.95 (s, 2H); 6.60 (d, 1H); 6.68 (d, 1H); 7.12–7.33 (m, 10H).

Mass (chemical ionization, isobutane, positive ions): 402 [M+1].

EXAMPLE 22

Preparation of (S)-N-[(6-amino-1-oxo)hexyl]-N-propyl-5,6-di(Phenylmethoxy)-1,2,3,4-tetrahydro-2-naphthylamine A solution of 6-phthalimidohexanoic acid chloride (11.2 g; 40.2 mmoles) in methylene chloride (60 ml) was added to a solution of (S)-N-propyl-5,6-di(phenylmethoxy)-1,2,3,4-tetrahydro-2-naphthylamine hydrochloride (16 g; 36.5 mmoles), prepared as described in example 21, and triethylamine (9.2 g; 91.3 mmoles) in methylene chloride (130 ml) kept under stirring at room temperature.

The reaction mixture was kept under stirring at room temperature for 1 hour.

After addition of water (200 ml), the phases were separated.

The organic phase was washed with water (100 ml), dried on anhydrous sodium sulphate and the solvent evaporated under reduced pressure.

The resultant residue was dissolved in a 33% solution of methylamine in ethanol (240 ml).

The reaction mixture was kept under stirring at room temperature for 6 hours, then evaporated to dryness under reduced pressure and the resultant residue was purified by column chromatography on silica gel (230–400 mesh), eluent methylene chloride:methanol:30% ammonia =90:10:1.

(S)-N-[(6-amino-1-oxo)hexyl]-N-propyl-5,6-di(phenylmethoxy)-1,2,3,4-tetrahydro-2-naphthylamine (10.9 g) was obtained.

$^1$H-NMR (200 MHz, CDCl$_3$): δ (ppm): 0.81–0.95 (2t, 3H); 1.23–2.02 (m, 10H); 2.26–2.38 (m, 2H); 2.51–3.21 (m, 8H); 3.80–4.61 (m, 1H); 4.99 (2s, 2H); 5.09 (2s, 2H); 6.69–6.87 (m, 2H); 7.25–7.47 (m, 10H).

Mass (chemical ionization, isobutane, positive ions): 515 [M+1].

EXAMPLE 23

Preparation of (S)-N-propyl-N-[6-[2-(3-methoxy-2-pyridyloxy)ethylamino|hexyl]-5,6-di(phenylmethoxy)-1,2,3,4-tetrahydro-2-naphthylamine trihydrochloride A solution of (3-methoxy-2-pyridyloxy)acetic acid hydrochloride (1.3 g; 5.9 mmoles), prepared as described in example 7, and N,N'-carbonyldiimidazole (0.95 g; 5.9 mmoles) in methylene chloride (15 ml) was kept under stirring at room temperature for 1 hour.

Triethylamine (0.6 g; 5.9 mmoles) and a solution of (S)-N-[(6-amino-1-oxo)hexyl]-N-propyl-5,6-di(phenylmethoxy)-1,2,3,4-tetrahydro-2-naphthylamine (3 g; 5.9 mmoles), prepared as described in example 22, in methylene chloride (15 ml) were added.

The reaction mixture was kept under stirring at room temperature for 3 hours; then water (50 ml) was added and the phases were separated.

The organic phase was dried on anhydrous sodium sulphate and the solvent was evaporated under reduced pressure.

The resultant residue was dissolved in tetrahydrofuran (30 ml).

Borane-dimethylsulphide complex (3 g; 38.9 mmoles) was slowly added to the resultant solution under stirring and under nitrogen.

At the end of the addition, the reaction mixture was heated under reflux for 1.5 hours.

After cooling at 5° C., a solution of 37% hydrochloric acid in methanol (10.5 ml) was added.

The reaction mixture was again heated under reflux for 1 hour, then concentrated by distilling the solvents at atmospheric pressure and brought to dryness under reduced pressure.

The resultant residue was dissolved in methanol (20 ml); the solvent was evaporated under reduced pressure, methanol (20 ml) was added again and the solvent was evaporated to dryness.

The residue was dissolved in absolute ethanol (20 ml) and a 15% (w/v) solution of hydrochloric acid in ethyl ether (0.5 ml) was added.

After evaporation of the solvents, a crude which was purified by column chromatography on silica gel (230–400 mesh), eluent methylene chloride:methanol:50% formic acid=85:15:1, was obtained.

The resultant solid was dissolved in absolute ethanol (15 ml).

A 15% (w/v) solution of hydrochloric acid in ethyl ether was added up to clearly acid pH and the solvents were evaporated under reduced pressure.

(S)-N-propyl-N-[6-[2-(3-methoxy-2-pyridyloxy)ethylamino]hexyl]-5,6-di(phenylmethoxy)-1,2,3,4-tetrahydro-2-naphthylamine trihydrochloride (1.8 g) was obtained as a white amorphous solid.

¹H-NMR (200 MHz, CDCl₃): δ (ppm): 0.98 (t, 3H); 1.34–2.55 (m, 12H); 2.55–3.30 (m, 10H); 3.32–3.65 (m, 3H); 3.94 (s, 3H); 4.97 (s, 2H); 5.06 (m, 2H); 5.09 (s, 2H); 7.12–7.75 (m, 15H); 9.95–10.18 (broad signal, 2H); 11.48–11.51 (broad signal, 1H).

Mass (chemical ionization, isobutane, positive ions): 652 [M+1].

By working in a similar way, the following compound was prepared:
(S)-N-propyl-N-[6-[2-[(1-methyl-2-imidazolyl)thio] ethylamino]hexyl]-5,6-dimethoxy-1,2,3,4-tetrahydro-2-naphthylamine trihydrochloride.

¹H-NMR (200 MHz, D₂O) ): δ (ppm): 0.81 (t, 3H); 1.19–2.22 (m, 12H); 2.46–3.19 (m, 14H); 3.47–3.64 (m, 1H); 3.60 (s, 3H); 3.62 (s, 3H); 3.69 (s, 3H); 6.81 (s, 2H); 7.09 (d, 1H); 7.21 (d, 1H).

Mass (chemical ionization, isobutane, positive ions): 489 [M+1].

EXAMPLE 24

Preparation of (S)-N-propyl-N-[6-[2-(3-methoxy-2-pyridyloxy)ethylamino]hexyl]-5,6-dihydroxy-1,2,3,4tetrahydro-2-naphthylamine trihydrochloride (Compound 11)

A solution of (S)-N-propyl-N-[6-[2-(3-methoxy-2-pyridyloxy)ethylamino]hexyl]-5,6-di(sphenylmethoxy)-1,2,3,4-tetrahydro-2-naphthylamine trihydrochloride (1.8 g; 2.4 mmoles), prepared as described in example 23, in absolute ethanol (65 ml), acidified with concentrated hydrochloric acid (0.5 ml), was hydrogenated at room temperature in a Parr apparatus (2.7 atm) in the presence of 10% palladium on charcoal (50% water; 0.6 g) for 8 hours.

The catalyst was filtered and the solution was brought to dryness under reduced pressure.

The resultant crude was purified by column chromatography on silica gel (230–400 mesh), eluent methylene chloride:methanol:50% formic acid=85:15:1.

The resultant solid was dissolved in absolute ethanol (25 ml).

A 15% (w/v) solution of hydrochloric acid in ethyl ether was added up to clearly acid pH and the solvents were evaporated under reduced pressure.

Compound 11 (0.85 g) was obtained as a white amorphous solid.

¹H-NMR (200 MHz, D₂O) ): δ (ppm): 0.78 (t, 3H); 1.18–2.14 (m, 12H); 2.33–3.15 (m, 10H); 3.32 (m, 2H); 3.37–3.54 (m, 1H); 3.68 (s, 3H); 4.34–4.41 (m, 2H); 6.42–6.60 (m, 2H); 6.84–7.48 (m, 3H).

Mass (chemical ionization, isobutane, positive ions): 472 [M+1].

EXAMPLE 25

Preparation of (S)-N-propyl-N-[6-[2-(4-pyridylthio) ethylamino]hexyl]-5,6-di(phenylmethoxy)-1,2,3,4-tetrahydro-2-naphtylamine trihydrochloride Triethylamine (2.3 g; 22.5 mmoles) and a solution of (4-pyridylthio) acetyl chloride (2.8 g; 15 mmoles) in methylene chloride (15 ml) were added to a solution of (S)-N-[(6-amino-1-oxo)hexyl]-N-propyl-5,6-di(phenylmethoxy)-1,2,3,4-tetrahydro-2-naphthylamine (3.9 g; 7.5 mmoles), prepared as described in example 22, in methylene chloride (35 ml), kept under stirring at room temperature.

The reaction mixture was kept under stirring at room temperature for 1 hour; then water (50 ml) was added and the phases were separated.

The organic phase was washed with an aqueous sodium bicarbonate solution (30 ml), dried on anhydrous sodium sulphate and the solvent was evaporated under reduced pressure.

The resultant residue was dissolved in tetrahydrofuran (25 ml).

Borane-dimethylsulphide complex (3.6 g; 45.6 mmoles) was slowly added to the resultant solution under stirring and under nitrogen.

At the end of the addition, the reaction mixture was heated under reflux for 1.5 hours.

After cooling at 5° C., a solution of 37% hydrochloric acid (1.5 ml) in methanol (13 ml) was added.

The reaction mixture was again heated under reflux for 1 hour, then concentrated by distilling the solvents at atmospheric pressure and brought to dryness under reduced pressure.

The resultant residue was dissolved in methanol (25 ml); the solvent was evaporated under reduced pressure, methanol (25 ml) was added again and the solvent was evaporated to dryness.

The residue was dissolved in absolute ethanol (25 ml) and a 15% (w/v) solution of hydrochloric acid in ethyl ether (1 ml) was added.

After evaporation of the solvents, a crude which was purified by column chromatography on silica gel (230–400 mesh), eluent methylene chloride:methanol:50% formic acid=85:15:1, was obtained.

The resultant solid was dissolved in absolute ethanol (20 ml).

A 15% (w/v) solution of hydrochloric acid in ethyl ether was added up to clearly acid pH and the solvents were evaporated under reduced pressure.

(S)-N-propyl-N-[6-[2-(4-pyridylthio)ethylamino]hexyl]-5,6-di(phenylmethoxy)-1,2,3,4-tetrahydro-2-napthylamine trihydrochloride (3 g) was obtained as a white solid.

¹H-NMR (200 MHz, D₂O) ): δ (ppm): 0.78 (t, 3H); 1.12–2.06 (m, 12H); 2.20–3.49 (m, 15H); 4.72 (s, 2H); 4.95 (s, 2H); 6.75 (d, 1H); 6.87 (d, 1H); 7.11–7.37 (m, 10H); 7.64–8.34 (m, 4H).

Mass (chemical ionization, methane, positive ions): 638 [M+1].

EXAMPLE 26

Preparation of (S)-N-propyl-N-[6-[2-(4-pyridylthio) ethylamino]hexyl]-5,6-dihydroxy-1,2,3,4-tetrahydro-2-naphthylamine trihydrochloride (Compound 12)

Trimethylsilyl iodide (10.2 g; 51.2 mmoles) was added to a solution of (S)-N-propyl-N-[6-[2-(4-pyridylthio) ethylamino]hexyl]-5,6-di(phenylmethoxy)-1,2,3,4-tetrahydro-2-naphthylamine trihydrochloride (3 g; 4 mmoles), prepared as described in example 25, in methylene chloride (35 ml), under stirring at room temperature.

The reaction mixture was kept under stirring at room temperature for 2 hours; methanol (30 ml) was added and the solvents were evaporated under reduced pressure.

The resultant crude was purified by column chromatography on silica gel (230–400 mesh), eluent methylene chloride:methanol:50% formic acid=80:20:1.

The resultant solid was dissolved in absolute ethanol (20 ml).

A 15% (w/v) solution of hydrochloric acid in ethyl ether was added up to clearly acid pH and the solvents were evaporated under reduced pressure.

Compound 12 (2.1 g) was obtained as a white amorphous solid.

$^1$H-NMR (200 MHz, $D_2O$) ): δ (ppm): 0.80 (t, 3H); 1.20–1.75 (m, 10H); 1.47–2.15 (m, 2H); 2.36–3.57 (m, 15H); 6.48 (d, 1H); 6.61 (d, 1H); 7.66–8.33 (m, 4H).

Mass (chemical ionization, isobutane, positive ions): 458 [M+1].

EXAMPLE 27

Preparation of (S)-N-propyl-N-[6-[2-(3-hydroxy-isoxazol-5-yl)ethylamino]hexyl]-5,6-dimethoxy-1,2,3,4-tetrahydro-2-naphthylamine Under stirring at room temperature, (3-hydroxy-isoxazol-5-yl)acetic acid (1 g; 7.0 mmoles), prepared as described in J. Org. Chem., 4307 (1983), was added to a solution of (S)-N-[(6-amino-1-oxo)hexyl]-N-propyl-5,6-dimethoxy-1,2,3,4-tetrahydro-2-naphthylamine (2.5 g; 7.0 mmoles), prepared as described in example 14, and dicyclohexylcarbodiimide (1.5 g; 7.3 mmoles) in tetrahydrofuran (20 ml)

The reaction mixture was kept under stirring for 24 hours.

The solvent was evaporated under reduced pressure and water (30 ml) and ethyl acetate (30 ml) were added to the residue.

The phases were separated, the organic phase was dried on anhydrous sodium sulphate and the solvent was evaporated under reduced pressure.

The resultant residue was dissolved in tetrahydrofuran (30 ml).

Borane-dimethylsulphide complex (2.4 g; 29.4 mmoles) was slowly added to the resultant solution under stirring and under nitrogen.

At the end of the addition, the reaction mixture was heated under reflux for 1.5 hours.

After cooling at 5° C., a solution of 37% hydrochloric acid (1.3 ml) in methanol (10 ml) was added.

The reaction mixture was again heated under reflux for 1 hour, concentrated by distilling the solvents at atmospheric pressure and brought to dryness under reduced pressure.

The resultant residue was dissolved in methanol (20 ml); the solvent was distilled under reduced pressure, methanol (20 ml) was added and the solvent was distilled again up to dryness.

The residue was dissolved in absolute ethanol (20 ml) and a 15% (w/v) solution of hydrochloric acid (0.5 ml) was added.

After evaporation of the solvents, a crude which was purified by column chromatography on silica gel (230–400 mesh), eluent methylene chloride:methanol:50% formic acid=80:20:1, was obtained.

(S)-N-propyl-N-[6-[2-(3-hydroxy-isoxazol-5-yl)ethylamino]hexyl]-5,6-dimethoxy-1,2,3,4-tetrahydro-2-naphthylamine (1.8 g) was obtained as an oil.

$^1$H-NMR (200 MHz, $CDCl_3$): δ (ppm): 0.90 (t, 3H); 1.20–2.32 (m, 12H); 2.51–3.34 (m, 15H); 3.75 (s, 3H); 3.80 (s, 3H); 5.63 (s, 1H); 6.71 (d, 1H); 6.79 (d, 1H).

Mass (chemical ionization, ammonia, positive ions): 460 [M+1].

EXAMPLE 28

Preparation of (S)-N-propyl-N-[6-[2-(3-hdroxy-isoxazol-5-yl)ethylamino]hexyl]-5,6-dihydroxy-1,2,3,4tetrahydro-2-naphthylamine trihydrobromide (Compound 13)

Boron tribromide (2.7 g; 10.8 mmoles) was added to a solution of (S)-N-propyl-N-[6-[2-(3-hydroxy-isoxazol-5-yl) ethylamino]hexyl]- 5,6-dimethoxy-1,2,3,4-tetrahydro-2-naphthylamine (1.7 g; 3.7 mmoles), prepared as described in example 27, in methylene chloride (34 ml), kept under stirring at –5° C.

The temperature was left arise to the room value and the reaction mixture was kept at this temperature for 20 minutes.

After cooling again at –5° C., methanol (10 ml) was added.

The solvents were evaporated under reduced pressure and methanol (20 ml) was added to the resultant residue.

After evaporation of the solvent, the crude was purified by column chromatography on silica gel (230–400 mesh), eluent methylene chloride:methanol:50% formic acid= 80:20:1.

Compound 13 (0.6 g) was obtained as a white amorphous solid.

$^1$H-NMR (200 MHz, $D_2O$) ): δ (ppm): 0.79 (t, 3H); 1.18–2.18 (m, 12H); 2.38–3.24 (m, 14H); 3.43–3.58 (m, 1H); 5.79 (s, 1H); 6.48 (d, 1H); 6.60 (d, 1H).

Mass (electronic impact): M/e 270, 321, 432.

By working in a similar way, the following compound was prepared:

(S)-N-propyl-N-[6-[2-[(1-methyl-2-imidazolyl)thiolethyl] amino]hexyl]-5,6-dihydroxy-1,2,3,4-tetrahydro-2-naphthylamine trihydrobromide (Compound 14).

$^1$H-NMR (200 MHz, $D_2O$) ): δ (ppm): 0.81 (t, 3H); 1.23–2.19 (m, 12H); 2.39–3.23 (m, 14H); 3.47–3.62 (m, 1H); 3.76 (s, 3H); 6.51 (d, 1H); 6.63 (d, 1H); 7.36 and 7.41 (2d, 2H).

Mass (chemical ionization, isobutane, positive ions): 461 [M+1].

EXAMPLE 24

Evaluation of the affinity towards $D_1$ and $D_2$ receptors

Brains of Sprague-Dawley male rats (200–250 g) were removed and the membranes of striated tissues were prepared according to the method described by Billard et al. in Life Sciences, 35, 1885, (1984).

The tissues were homogenized in 50 mM Tris/HCl buffer at pH 7.4 (1:100 weight/volume).

The homogenate was centrifuged and the pellet resuspended, recentrifugated and resuspended again in 50 mM Tris/HCl buffer at pH 7.4 containing 120 mM NaCl, 5mM KCl, 2mM $CaCl_2$ and 1 mM $MgCl_2$.

The affinity towards $D_1$ receptor and $D_2$ receptor was evaluated by using [$^3$H]-SCH23390 [R(+)-8-chloro-2,3,4,5-tetrahydro-3-methyl-5-phenyl-1H-3-benzazepine 7-ol hydrochloride] and [$^3$H]-domperidone (The Merck Index—XI ed., no. 3412, page 537) respectively as labeled ligands.

As reference substances dopamine and dopexamine were used.

The conditions of standard incubation (volume 1000 µl) for the test in which [$^3$H]-SCH23390 was used were the following: 50 mM Tris/HCl buffer (pH 7.4), 0.2 nM [$^3$H]-SCH23390, a membrane preparation of 130–140 µg proteins/ml.

The mixture was incubated with different concentrations of the tested compounds at 37° C. for 20 minutes, filtered under vacuum through Whatman GF/C filters and then washed 4 times with 5 ml of 50 mM Tris/HCl buffer (pH 7.4) cooled with ice.

For the affinity studies towards $D_2$ receptor, [$^3$H]-domperidone (0.3 nM) was incubated in a volume of 1000 µl containing buffer and membrane preparation as above described.

Furthermore, bovine serum albumine (BSA) (0.01%) was added.

The mixture was incubated at 37° C. for 30 minutes for each concentration of tested compounds.

The obtained results, expressed as $K_i$, (nM), for some representative compounds of formula I, dopamine and dopexamine are reported in the following table.

TABLE 1

Affinity [$K_i$ (nm)] of compounds 1, 2, 3, 5, 6, 7, 8, 9, 10, 11, 12, 13, dopamine and dopexamine towards $D_1$ and $D_2$ receptors determined by binding studies on rat striated membranes.

| | $D_1$ [$^3$H]-SCH23390 | $D_2$ [$^3$H]-domperidone |
|---|---|---|
| Compound 1 | 24 | 0.27 |
| Compound 2 | 32 | 1.2 |
| Compound 3 | 29 | 0.7 |
| Compound 5 | 133 | 2.3 |
| Compound 6 | 75 | 0.9 |
| Compound 7 | 23 | 0.5 |
| Compound 8 | 25 | 0.4 |
| Compound 9 | 113 | 0.6 |
| Compound 10 | 43 | 0.6 |
| Compound 11 | 65 | 0.3 |
| Compound 12 | 57 | 1.1 |
| Compound 13 | 412 | 2.7 |
| Dopamine | 3200 | 1500 |
| Dopexamine | 3200 | 1220 |

The compounds of formula I, object of the present invention, show a high affinity towards both receptor subtypes resulting at least 10 times more potent than dopamine and dopexamine on $D_1$ and $D_2$ receptors.

EXAMPLE 25

Evaluation of in vivo antihypertensive activity

Male SHR rats, 3–4 months old, fasted 16 hours before the experiment were used. Systolic blood pressure (SBP) and heart rate (HR) were recorded by tail cuff method in conscious animals by means of a BP Recorder (W+W Basile, Italy). Before each pressure determination, animals were maintained at 37° C. for 10 minutes.

SBP and HR values were recorded before and at different times up to seven hours after the treatment with the tested compounds.

The compounds were administered orally by gavage (volume 10 ml/kg) at doses between 10 and 160 mg/kg. For the administration, the compounds were suspended in carboxymethylcellulose (CMC) 0.5% in water and additioned with Tween 80$^R$ (0.3 ml/10 ml of CMC).

The results of the evaluation of the in vivo antihypertensive activity have been expressed as $ED_{25mmHg}$ (mg/kg p.o.), that is the dose causing a 25mmHg decrease of SBP basal value.

The obtained $ED_{25mmHg}$ value for Compound 1 was the following: Compound 1: $ED_{25mmHg}$=80 mg/kg p.o.

The administration of Compound 1 did not cause any significant change in the HR of the animals.

Similar results were obtained with other compounds of formula I.

We claim:

1. A compound of formula

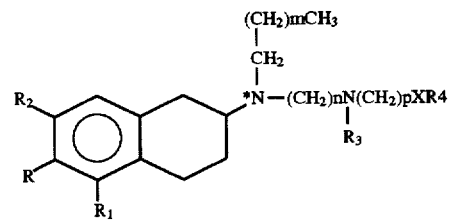

wherein

R is a hydrogen atom or an OY group;

$R_1$ is a hydrogen atom or an OY' group, $R_2$ is a hydrogen atom or an OY" group;

provided that at least one of R, $R_1$ and $R_2$ is hydrogen but R, $R_1$ and $R_2$ are not contemporaneously hydrogen atoms and $R_1$ and $R_2$ are not contemporaneously OY' or OY" groups respectively;

Y, Y' and Y", the same or different, are a hydrogen atom or an acyl group derived from an optionilly substituted aliphatic, aromatic or heteroaromatic carboxylic acid, from an optionally substituted carbonic or carbamic acid or for a phosphoric acid of the formula

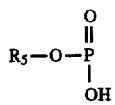

wherein $R_5$ is a hydrogen atom, a $C_1$–$C_6$ alkyl optionally substituted by one or more groups selected from the group consisting of hydroxy, alkoxy, acyloxy, amino, carboxy and alkoxycarbonyl; or a phenyl;

m is an integer selected from 1 or 2;

n is 3 to 8;

P is an integer of 2 to 4;

$R_3$ is a hydrogen atom or a $C_1$–$C_4$ alkyl;

$R_4$ is a phenyl optionally substituted by halogen atoms $C_1$–$C_3$ alkyl or alkoxy groups; or a 5- or 6-membered heteroaryl containing one or more heteroatoms selected from the group consisting of oxygen, nitrogen and sulphur, optionally substituted by halogen atoms, hydroxy groups, $C_1$–$C_3$ alkyl or alkoxy groups;

X is NH, S, SO, $SO_2$, CO, $CF_2$, or O; provided that when X is O, $R_4$, is different from phenyl; the asterisk marks an asymmetric carbon atom; and pharmaceutically acceptable salts thereof.

2. A compound according to claim 1 wherein R is OY, $R_1$ is OY'; Y, Y' and $R_2$ are hydrogen atoms, and n is an integer of 5, 6 or 7.

3. A compound according to claim 1 wherein R is OY, $R_1$ is OY'; Y, Y' and $R_2$ are hydrogen atoms, n is 6, m is 1, p is 2 or 3, X is S, CO or NH, $R_4$ is phenyl optionally substituted by one or two methyl, methoxy, or chloro groups.

4. A compound according to claim 1 wherein R is OY, $R_1$ is OY'; Y, Y' and $R_2$ are hydrogen atoms, n is 6, m is 1, p is 2, X is S or O, $R_4$ is a heteroaryl selected from the group consisting of thienyl, pyridyl, imidazolyl and isoxazolyl, optionally substituted by a hydroxy, methyl or methoxy group.

5. A compound according to claim 1 wherein one or two of Y, Y' and Y", are the same or different, and are acyl groups derived from acetic, propionic, butyric, isobutyric acid, from optionally substituted benzoic or pyridinecarboxylic acid, from phosphoric, carbamic or carbonic acid.

6. A compound according to claim 1 in optically active form.

7. A compound according to claim 1 in which the carbon atom marked by an asterisk has (S) configuration.

8. A process for the preparation of a compound according to claim 1 which comprises the reduction of a compound of the formula

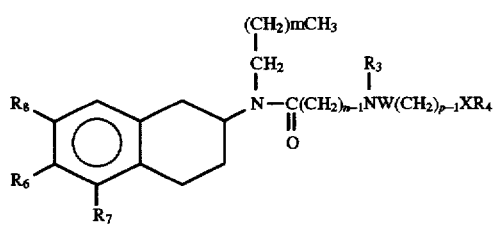

wherein m, n, p, X, $R_3$ and $R_4$ have the meaning reported in claim 1;

$R_6$ is a hydrogen atom or an OY''' group wherein Y''' is a hydrogen atom or a protecting group selected from the group consisting of methyl, benzyl, benzoyl and 4-methoxy-benzoyl;

$R_7$ and $R_8$ are the same or different and are a hydrogen or an OY''' group; provided that at least one of $R_6$, $R_7$ and $R_8$ is a hydrogen atom but $R_6$, $R_7$ and $R_8$ are not contemporaneously hydrogen atoms and $R_7$ and $R_8$ are not contemporaneously OY''' groups; and W is a $CH_2$ or CO group.

9. A pharmaceutical composition containing a therapeutically effective amount of a compound according to claim 1 in admixture with a suitable carrier.

10. A pharamaceutical composition according to claim 9 for the treatment of cardiovascular diseases.

* * * * *